United States Patent
Smokvina et al.

(10) Patent No.: US 11,207,358 B2
(45) Date of Patent: Dec. 28, 2021

(54) **PROBIOTIC COMPOSITION COMPRISING *LACTOBACILLUS RHAMNOSUS* AND *LACTOBACILLUS PARACASEI* AND METHODS THEREOF**

(71) Applicant: COMPAGNIE GERVAIS DANONE, Paris (FR)

(72) Inventors: Tamara Smokvina, Orsay (FR); Rebeca Martin Rosique, Jouy en Josas (FR); Philippe Langella, Velisy (FR)

(73) Assignee: COMPAGNIE GERVAIS DANONE, Paris (FR)

( * ) Notice: Subject to any disclaimer, the term of this patent is extended or adjusted under 35 U.S.C. 154(b) by 37 days.

(21) Appl. No.: 16/468,520

(22) PCT Filed: Dec. 16, 2016

(86) PCT No.: PCT/IB2016/002022
§ 371 (c)(1),
(2) Date: Jun. 11, 2019

(87) PCT Pub. No.: WO2018/109520
PCT Pub. Date: Jun. 21, 2018

(65) Prior Publication Data
US 2020/0078420 A1    Mar. 12, 2020

(51) Int. Cl.
*A61K 35/747* (2015.01)
*A23L 33/135* (2016.01)
*A61P 1/00* (2006.01)
*A23C 9/123* (2006.01)
*C12N 1/20* (2006.01)
*A61K 35/00* (2006.01)
*C12R 1/225* (2006.01)

(52) U.S. Cl.
CPC .......... *A61K 35/747* (2013.01); *A23C 9/1234* (2013.01); *A23L 33/135* (2016.08); *A61P 1/00* (2018.01); *C12N 1/20* (2013.01); *C12N 1/205* (2021.05); *A23V 2002/00* (2013.01); *A23Y 2220/63* (2013.01); *A23Y 2220/73* (2013.01); *A61K 2035/115* (2013.01); *C12R 2001/225* (2021.05)

(58) Field of Classification Search
CPC . A23C 9/1234; A23L 33/135; A23Y 2220/63; A23Y 2220/73; A61P 29/00; A61P 31/00; A61P 31/04; A61P 1/00; A61P 37/00; C12N 1/20; C12N 1/205; C12R 1/225; C12R 1/25; C12R 2001/225; A61K 2035/115; A61K 35/747; A61K 2035/11; A61K 35/74; A61K 35/741; A23V 2002/00

See application file for complete search history.

(56) References Cited

U.S. PATENT DOCUMENTS

| | | | |
|---|---|---|---|
| 8,557,561 B2 * | 10/2013 | Chambaud | A61P 29/00 435/252.9 |
| 2011/0150852 A1 * | 6/2011 | Chambaud | A23C 9/1234 424/93.45 |
| 2013/0202738 A1 | 8/2013 | Daval et al. | |
| 2017/0028000 A1 * | 2/2017 | Grompone | A61P 31/04 |
| 2020/0078420 A1 * | 3/2020 | Smokvina | A23L 33/135 |

FOREIGN PATENT DOCUMENTS

| | | |
|---|---|---|
| KR | 20130002545 A | 1/2013 |
| WO | 2012136830 A1 | 10/2012 |

OTHER PUBLICATIONS

Coman et al., "Functional Foods as Carriers for SYNBIO, a Probiotic Bacteria Combination," International Journal of Food Microbiology, vol. 157, No. 3, 2012, pp. 346-352.
Verdenelli et al., "Influence of a Combination of Two Potential Probiotic Strains, Lactobacillus rhamnosus IMC 501 and Lactobacillus Paracasei IMC 502 on Bowl Habits of Healthy Adults," Letters in Applied Microbiology, vol. 52, No. 6, Jun. 2011, pp. 596-602.
Wen-Hsin et al., "Induced Apoptosis of Th2 Lymphocytes and Inhibition of Airway Hyperresponsiveness and Inflammation by combined lactic acid bacteria treatment," International Immunopharmacology, vol. 15, No. 4, 2013, pp. 703-711.
International Search Report issued in PCT/IB2016/002022, dated Jun. 30, 2017.

* cited by examiner

Primary Examiner — Deborah K Ware
(74) Attorney, Agent, or Firm — Arent Fox LLP

(57) ABSTRACT

The present invention relates to a composition comprising a given *Lactobacillus rhamnosus* strain and a given *Lactobacillus paracasei* strain wherein the ratio of the given *Lactobacillus rhamnosus* strain to the given *Lactobacillus paracasei* strain (LRα:LPα) is higher or equal to 8:1 and to methods thereof.

10 Claims, 1 Drawing Sheet

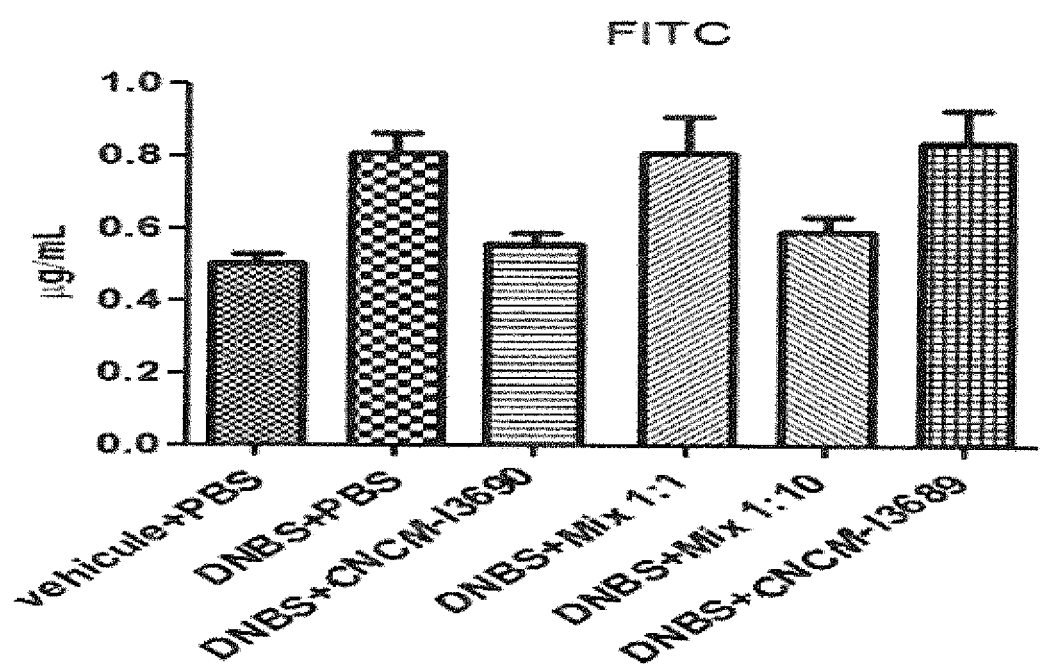

PROBIOTIC COMPOSITION COMPRISING LACTOBACILLUS RHAMNOSUS AND LACTOBACILLUS PARACASEI AND METHODS THEREOF

CROSS REFERENCE TO RELATED APPLICATIONS

This application is a 35 U.S.C. 371 National Phase of PCT Application No. PCT/IB2016/002022 filed Dec. 16, 2016, the disclosure of which is hereby incorporated by reference in its entirety.

FIELD OF THE INVENTION

The present invention relates to the field of probiotics. In particular, the present invention relates to a probiotic composition comprising one given *Lactobacillus rhamnosus* strain and one given *Lactobacillus paracasei* strain. The present invention also relates to the use of this composition in a method of prevention and to the process for preparing this composition.

BACKGROUND OF THE INVENTION

For a long time health benefits have been assigned to some fermented food products such as yogurt, ranging from improved nutrient uptake/availability due to the fermentation, to specific effects assigned to the bacteria strains themselves.

These live microorganisms which when administered in adequate amounts confer a health benefit on the host are generally referred to as probiotics. Most of the microorganisms used as probiotics are lactic acid bacteria, in particular strains from *Lactobacillus* and *Bifidobacteria* genus.

Many studies have been done to clinically investigate the health benefits of the lactic acid strains.

At first, lactic acid strains were thought to beneficially affect the host mainly by improving its intestinal microbial balance, through competition with pathogens and toxin-producing bacteria.

In particular, it was shown probiotics prevent or treat intestinal infections (Foster et al., 2011; Pamer, 2014). Such approaches were also associated with higher clearance of intestinal antibiotic-resistant infection in mice (Vidal et al., 2010).

Now, it has also been shown that the health benefits of probiotics go beyond the intestinal microbial balance. They also include alleviation of chronic intestinal inflammatory diseases, prevention and treatment of pathogen-induced diarrhea, urogenital infections, atopic diseases etc. For instance, the *Escherichia coli Nissle* 1917, *Lactobacillus rhamnosus* GG (LGG) and *Lactobacillus rhamnosus* CNCM I-3690 have been shown to prevent the increase in intestinal permeability in vivo (Ukena et al., 2007, Donato et al. 2010 and Laval L et al., 2015).

The health benefits of probiotics being different from one strain to another, research is emerging on compositions comprising multiple probiotics species. However, the behavior of one strain can be influenced by the presence of another strain. Indeed, due to the competition and/or interactions between some these bacteria or the metabolites they produce, it is not always possible to provide a composition comprising several probiotics.

Actually, most studies on probiotics use single strains. There are fewer studies on efficacy of mixtures of probiotic strains. And when such studies have been carried out the evidence that mixtures are more effective than their component strains is limited (Chapman et al., 2011).

DETAILED DESCRIPTION OF THE INVENTION

The inventors have surprisingly found a very effective multiple strains composition which comprises an appropriate ratio of a given *Lactobacillus rhamnosus* strain to a given *Lactobacillus paracasei* strain. This multiple strains composition prevents notably the increase in the gut permeability.

A subject of the present invention is therefore a composition comprising:
- a given *Lactobacillus rhamnosus* strain and
- a given *Lactobacillus paracasei* strain wherein the ratio of said given *Lactobacillus rhamnosus* strain to said given *Lactobacillus paracasei* strain ($LR_\alpha:LP_\alpha$) is higher or equal to 8:1.

The ratio $LR_\alpha:LP_\alpha$ may be determined in different way. For example, it may be determined based on the Colony Forming Unit of the given *Lactobacillus rhamnosus* strain and the Colony Forming Unit of the given *Lactobacillus paracasei* strain in the composition. It may also be based on the CFU of each of the given strains per gram of dry weight of the composition or based on the CFU of each of the given strains per volume of composition.

The ratio $LR_\alpha:LP_\alpha$ may be higher or equal to 9:1, higher or equal to 10:1 or higher or equal to 11:1.

In one embodiment, the ratio $LR_\alpha:LP_\alpha$ is strictly higher than 10:1. Preferably, the ratio $LR_\alpha:LP_\alpha$ is equal to 10:1.

The ratio $LR_\alpha:LP_\alpha$ is lower than 20:1, lower than 17:1 or lower than 15:1.

Preferably, the ratio $LR_\alpha:LP_\alpha$ is between 9:1 and 15:1, more preferably between 10:1 and 12:1.

In a preferred embodiment, the composition comprises at least $10^6$ Colony Forming Unit per ml (CFU/ml) of said given *Lactobacillus rhamnosus* strain, preferably between $10^8$ CFU/ml and $10^{10}$ CFU/ml, more preferably $10^9$ CFU/ml.

Since the ratio $LR_\alpha:LP_\alpha$ is known, it is easy to determine the concentration of said given *Lactobacillus paracasei* strain based on the concentration of said given *Lactobacillus rhamnosus* strain. For example, if the given *Lactobacillus rhamnosus* strain is at $10^9$ CFU/ml in the composition and the ratio $LR_\alpha:LP_\alpha$ is 10:1. Then, the given *Lactobacillus paracasei* strain is at $10^8$ CFU/ml in the composition.

In a preferred embodiment, the composition comprises at least $10^5$ CFU/ml of said given *Lactobacillus paracasei* strain, preferably between $10^7$ CFU/ml and $10^9$ CFU/ml, more preferably $10^8$ CFU/ml.

Typically, said given *Lactobacillus rhamnosus* strain is a probiotic strain which regulates the gut barrier function.

In a preferred embodiment, said given *Lactobacillus rhamnosus* strain is selected from the group consisting of *Lactobacillus rhamnosus* CNCM I-3690 and *Lactobacillus rhamnosus* GG (ATCC 53103).

The *Lactobacillus rhamnosus* CNCM I-3690 was disclosed WO2009/130423 and was deposited, according to the Budapest Treaty, at CNCM (Collection Nationale de Cultures de Microorganismes, 25 rue du Docteur Roux, Paris, France) on Nov. 19, 2006 with the number 1-3690.

The *Lactobacillus rhamnosus* GG (ATCC 53103) (LGG®) is disclosed in U.S. Pat. No. 4,839,281 and was deposited, according to the Budapest Treaty, at ATCC (American Type Culture Collection (ATCC) 10801 University Blvd. Manassas, Va. 20110-2209 United States of America) with the number 53103.

The *Lactobacillus rhamnosus* strains which can be obtained by mutagenesis or by genetic transformation of above mentioned given *Lactobacillus rhamnosus* strain and which keep their probiotic properties are also encompassed in the present invention. Preferably, the *Lactobacillus rhamnosus* strain is *Lactobacillus rhamnosus* CNCM I-3690.

Typically, said given *Lactobacillus paracasei* is a probiotic strain with immunomodulatory properties. In a preferred embodiment, said given *Lactobacillus paracasei* strain is selected from the group consisting of *Lactobacillus paracasei* CNCM I-3689 and *Lactobacillus paracasei* CNCM I-1518.

The *Lactobacillus paracasei* CNCM I-3689 is disclosed in WO2009122042 and was deposited, according to the Budapest Treaty, at CNCM on Nov. 9, 2006 with the reference CNCM I-3689.

The *Lactobacillus paracasei* CNCM I-1518 is disclosed in EP0794707 and was deposited, according to the Budapest Treaty, at CNCM on Sep. 28, 1994 with the reference CNCM I-1518.

The *Lactobacillus paracasei* CNCM I-3689 and *Lactobacillus paracasei* CNCM I-1518 both have immuno-modulatory properties (see notably WO2009/130423).

As for the given *Lactobacillus rhamnosus* strains, the *Lactobacillus paracasei* strains which can be obtained by mutagenesis or by genetic transformation of *Lactobacillus paracasei* CNCM I-3689 and *Lactobacillus paracasei* CNCM I-1518 strain which keep its probiotic properties are also encompassed in the present invention.

In a more preferred embodiment, the composition comprises a given *Lactobacillus rhamnosus* strain which is *Lactobacillus rhamnosus* CNCM I-3690 and a given *Lactobacillus paracasei* strain which is *Lactobacillus paracasei* CNCM I-3689. The ratio of the given *Lactobacillus rhamnosus* strain which is *Lactobacillus rhamnosus* CNCM I-3690 to the given *Lactobacillus paracasei* strain which is *Lactobacillus paracasei* CNCM I-3689 ($LR_\alpha:LP_\alpha$) is as mentioned hereinabove, for example higher or equal to 8:1, higher or equal to 9:1, higher or equal to 10:1 or higher or equal to 11:1.

In another embodiment, the composition comprises a given *Lactobacillus rhamnosus* strain which is *Lactobacillus rhamnosus* CNCM I-3690 and a given *Lactobacillus paracasei* strain which is *Lactobacillus paracasei* CNCM I-1518. The ratio of the given *Lactobacillus rhamnosus* strain which is *Lactobacillus rhamnosus* CNCM I-3690 to the given *Lactobacillus paracasei* strain which is *Lactobacillus paracasei* CNCM I-1518 ($LR_\alpha:LP_\alpha$) is as mentioned hereinabove, for example higher or equal to 8:1, higher or equal to 9:1, higher or equal to 10:1 or higher or equal to 11:1.

In yet another embodiment, the composition comprises a given *Lactobacillus rhamnosus* strain which is *Lactobacillus rhamnosus* CNCM I-3690, a first given *Lactobacillus paracasei* strain which *Lactobacillus paracasei* CNCM I-3689 and a second given *Lactobacillus paracasei* strain which is *Lactobacillus paracasei* CNCM I-1518. The ratio of the given *Lactobacillus rhamnosus* strain which is *Lactobacillus rhamnosus* CNCM I-3690 to the first given *Lactobacillus paracasei* strain which *Lactobacillus paracasei* CNCM I-3689 ($LR_\alpha:LP_{\alpha1}$) is as mentioned hereinabove, for example higher or equal to 8:1, higher or equal to 9:1, higher or equal to 10:1 or higher or equal to 11:1.

And the ratio of the given *Lactobacillus rhamnosus* strain which is *Lactobacillus rhamnosus* CNCM I-3690 to the second given *Lactobacillus paracasei* strain which *Lactobacillus paracasei* CNCM I-1518 ($LR_\alpha:LP_{\alpha2}$) is also as mentioned hereinabove, for example higher or equal to 8:1, higher or equal to 9:1, higher or equal to 10:1 or higher or equal to 11:1.

The composition can further comprise other strains of *Lactobacillus* and/or other strains of bacteria than the given *Lactobacillus rhamnosus* or the given *Lactobacillus paracasei*.

For example, the composition may comprise various ferments which can be used for performing the fermentation of the dairy product and in particular a culture of lactic acid bacteria such as:

*Lactobacillus* sp. (for ex. *Lactobacillus bulgaricus*, *Lactobacillus acidophilus*, *Lactobacillus pentosus*, *Lactobacillus helveticus*, *Lactobacillus reuteri*, *Lactobacillus plantarum*, *Lactobacillus bifidus* and combinations thereof),

*Lactococcus* sp. (for ex. *Lactococcus lactis*),

*Bifidobacterium* sp. (for ex. *Bifidobacterium bifidum*, *Bifidobacterium infantis*, *Bifidobacterium animalis*, especially *Bifidobacterium animalis* subsp. *lactis*, *Bifidobacterium breve*, *Bifidobacterium longum* and combinations thereof), and/or

*Streptococcus* sp. (for ex. *Streptococcus thermophilus*, *Streptococcus lactis*, *Streptococcus raffinolactis*, *Streptococcus cremoris* and combinations thereof).

Preferred lactic acid bacteria to be used in the present invention in particular to obtain a fermented dairy composition are selected from *Lactobacillus bulgaricus*, *Streptococcus thermophilus*, *Lactococcus lactis*, *Bifidobacterium animalis* subsp. *lactis*, and combinations thereof.

In an embodiment, the composition comprises at least one additional *Lactobacillus paracasei* strain. The additional *Lactobacillus paracasei* differs from said given *Lactobacillus paracasei* strain. Said at least additional *Lactobacillus paracasei* strain may be for example the *Lactobacillus paracasei* CNCM I-1518 (with the proviso that the given *Lactobacillus paracasei* strain is not *Lactobacillus paracasei* CNCM I-1518). When the composition comprises such additional *Lactobacillus paracasei* strain, the additional *Lactobacillus paracasei* strain is not took in consideration in the ratio $LR_\alpha:LP_\alpha$.

For example, if the composition comprises a given *Lactobacillus rhamnosus* strain which is *Lactobacillus rhamnosus* CNCM I-3690, a given *Lactobacillus paracasei* strain which is *Lactobacillus paracasei* CNCM I-3689 and an additional *Lactobacillus paracasei* strain which *Lactobacillus paracasei* is *Lactobacillus paracasei* CNCM I-1518, the $LR_\alpha:LP_\alpha$ ratio is the ratio of *Lactobacillus rhamnosus* CNCM I-3690 to *Lactobacillus paracasei* CNCM I-3689. The *Lactobacillus paracasei* CNCM I-1518 is not took in consideration in this ratio. The ratio *Lactobacillus rhamnosus* CNCM I-3690 to *Lactobacillus paracasei* CNCM I-1518 ($LR_\alpha:LP_\beta$) may be different from the $LR_\alpha:LP_\alpha$ ratio. For example, the $LR_\alpha:LP_\alpha$ ratio may be 10:1 and the $LR_\alpha:LP_\beta$ ratio may be 1:1. According to the present invention, the composition can be in a form suitable for oral administration. This includes for instance solids, semisolids, liquids, and powders. Semi-solid compositions, such as yogurts, and liquid compositions, such as drinks, are preferred.

The composition can be a pharmaceutical composition or a nutritional composition. According to a preferred embodiment, the composition is a nutritional composition such as a food product (including a functional food) or a food supplement, A "food, supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular food supplements and functional food can have a physiological effect—protective or curative—against a disease, for example against a chronic disease.

According to the invention, the composition may be a dairy product, preferably a fermented dairy product.

In the context of the present invention, "fermented dairy product" designates more particularly a fermented dairy product ready for human consumption, such as a fermented milk, a yoghurt, or a fresh cheese such as a white cheese or a petit-suisse. It can be also a strained fermented dairy product such as a strained yoghurt also called concentrated yoghurt or Greek-style yoghurt.

The terms "fermented milk" and "yoghurt" are given their usual meanings in the field of the dairy industry, that is, products destined for human consumption and originating from acidifying lactic fermentation of a milk substrate. These products can contain secondary ingredients such as fruits, vegetables, sugar, etc.

The expression "fermented milk" is thus reserved in the present application for a dairy product prepared with a milk substrate which has undergone treatment at least equivalent to pasteurisation, seeded with microorganisms belonging to the characteristic species or species of each product.

The term "yoghurt" is reserved for fermented milk obtained, according to local and constant usage, by the development of specific thermophilic lactic bacteria known as *Lactobacillus delbrueckii* subsp. *bulgaricus* and *Streptococcus thermophilus*, which must be in the living state in the finished product, at a minimum rate. In certain countries, regulations require the addition of other lactic bacteria to the production of yoghurt, and especially the additional use of strains of *Bifidobacterium* and/or *Lactobacillus acidophilus* and/or *Lactobacillus casei*. These lactic strains are intended to impart various properties to the finished product, such as that of favouring equilibrium of intestinal flora or modulating the immune system. The yoghurt can be a stirred or set yoghurt.

In practice, the expression "fermented milk" is therefore generally used to designate fermented milks other than yoghurts. It can also, according to country, be known by names as diverse as, for example, "Kefir", "Kumtss", "Lassi", "Dahi", "Leben", "Filmjolk", "Acidophilus milk".

Finally, the name "white cheese" or "petit-Suisse" is, in the present application, reserved for unrefined non-salty cheese, which has undergone fermentation by lactic bacteria only (and no fermentation other than lactic fermentation).

The fermented dairy product is made from whole milk and/or wholly or partly skimmed milk, which can be used in a powder form which can be reconstituted by addition of water. Other milk components can be added such as cream, casein, caseinate (for ex. calcium or sodium caseinate), whey proteins notably in the form of a concentrate (WPC), milk proteins notably in the form of a concentrate (MPC), milk protein hydrolysates, and mixtures thereof.

The milk and milk components has typically an animal origin such as a cow, goat, sheep, buffalo, donkey or camel origin.

The fermented dairy product contains a texturizing agent that is to say an agent used to modify the overall texture or mouthfeel of a food product, such as gelling agents (for ex. gelatine, agar, carrageenan, pectin, natural gums), stabilisers (for ex. starch, agar, pectin, gum, Arabic gelatin), thickeners (for ex. guar gum, xanthan gum, pectin, starch, agar, carrageenan, alginic acid). It can be more particularly a gelling agent such as gelatine, agar, carrageenan, or pectin, in particular gelatine, agar, or carrageenan. Other food additives can be present, in addition to the texturizing agent, notably chosen among:

sugars and sweeteners:
sugars and sweeteners are food-acceptable carbohydrate sweetening agents that may be natural or artificial, no or low calorie sweeteners;
preferred examples of appropriate sugars are sucrose, fructose, lactose, glucose and maltose. Such sugars can be incorporated in the form of beet sugar, cane sugar, maple sugar, molasses, corn syrup, malt syrup, maple syrup, agave nectar or also honey;
preferred examples of appropriate no or low calorie sweeteners are aspartame, sucralose, acesulfame potassium, saccharin, sodium cyclamate, thaumatin, tagatose, neohesperidin dihydrochalcone, isomaltulose, rebaudioside A or also a *stevia* extract (containing rebaudioside A),
vitamins (e.g. vitamin A, B1, B2, B6, B12, C, D, E or K, folic acid, etc.),
anti-oxidants,
pH-modifying agents (e.g. buffering agents or acidifying agents such as citric acid and its salts, for ex. sodium, potassium or calcium citrate),
lubricants (e.g. vegetable oils),
preservatives (e.g. sorbic acid and its salts such as sodium, potassium and calcium salts, sulphur dioxide, benzoic acid and its salts such as sodium, potassium and calcium salts, ethyl, methyl or propyl p-hydroxybenzoate, etc.),
taste exhausters (e.g. glutamic acid and its salts such as sodium, potassium, calcium, magnesium or ammonium salts),
flavouring aromatic agents of synthetic or natural origin (e.g. fruit flavours), and
colouring agents (pigments, dyes, etc.).

If need be, the skilled artisan will be able to choose appropriate food additives among all the well-known food additives and excipients available on the market.

The composition of the invention may also a fermented product which is fermented vegetable, such as fermented soy, cereals and/or fruits in set, stirred or drinkable forms.

The fermented product can be in the form of a liquid or in the form of a dry powder obtained by drying the fermented liquid. Nutritional compositions which can be used according to the invention also include baby foods, infant milk formulas and infant follow-on formulas. In a preferred embodiment, the fermented product is a fresh product. A fresh product, which has not undergone severe heat treatment steps, has the advantage that the bacterial strains present are in the living form.

The present invention also relates to a composition of the invention for use in a method for prevention or treatment of the human or animal body.

The present invention relates to a method for prevention or treatment in a subject in need thereof comprising administering to said subject an effective amount of the composition of the invention.

In a preferred embodiment, the composition of the invention is for use in improving the intestinal epithelial barrier integrity. Indeed, as previously mentioned said given *Lactobacillus rhamnosus* strain is typically a probiotic strain which regulates the gut barrier function.

The intestinal barrier dysfunction is an important factor in the clinical manifestation of a wide number of disorders and diseases such as irritable bowel syndrome (IBS), food allergies, type-1 diabetes, obesity (Camilleri M L K et al., 2012, Perrier C C B. et al. 2011, Vaarala O., 2012) and precedes chronic inflammation processes such as inflammatory bowel diseases (IBD) (Vetrano S. et al, 2011).

Thus, the composition of the invention may be for use in preventing or treating a disorder selected from the group consisting of a gastrointestinal disorder, type 1 diabetes and obesity. In particular, the gastrointestinal disorder may be an inflammatory bowel disease (IBD) and/or irritable bowel syndrome (IBS).

Owing to the immune-modulatory properties of said given *Lactobacillus paracasei* strain, the composition may also be for use as immunomodulatory composition.

Preferably, the composition of the invention is for use both as immunomodulatory composition and in preventing or treating a disorder selected from the group consisting of a gastrointestinal disorder, type 1 diabetes and obesity.

The present invention relates to a method for preventing or treating a disorder selected from the group consisting of a gastrointestinal disorder, type 1 diabetes and obesity in a subject in need thereof comprising administering to said subject an effective amount of the composition of the invention.

The present invention also relates to a process for preparing a composition of the invention.

Probiotic compositions comprising multiple strains are classically obtained by growing separately each probiotic strain to be used in the composition under conditions suitable for the growth of said strain, and adding them to the final product after their growth is completed.

Thus, in an embodiment, the process for preparing the composition of the invention comprises the step of adding to a medium a given *Lactobacillus rhamnosus* strain and a given *Lactobacillus paracasei* strain. The given *Lactobacillus rhamnosus* strain and the given *Lactobacillus paracasei* strain are grown separately each under conditions suitable for the growth of the strain. Then after their growth is completed, said given *Lactobacillus rhamnosus* strain and said given *Lactobacillus paracasei* strain are added to a medium so that to obtain the desired the $LR_\alpha:LP_\alpha$ ratio, thereby resulting in the composition of the invention. If the medium does not already comprise said given *Lactobacillus rhamnosus* strain and said given *Lactobacillus paracasei*, said given *Lactobacillus rhamnosus* strain and said given *Lactobacillus paracasei* strain may be added to a medium at the desired the ratio $LR_\alpha:LP_\alpha$.

Another way to prepare multiple strains probiotic compositions is the co-fermentation also called co-culturing.

In this embodiment, the process for preparing the composition of the invention comprises the steps of:
  inoculating a fermentation medium with said given *Lactobacillus rhamnosus* strain and said given *Lactobacillus paracasei* strain and
  fermenting the inoculated medium by incubating it at a temperature suitable for growth of said strains. The fermentation is stopped when the desired the $LR_\alpha:LP_\alpha$ ratio is reached.

The main advantage of the co-fermentation is that the metabolites released by the strains during the fermentation remain in the final product i.e. in the composition of the invention.

The present invention also relates to a process for preparing a composition comprising the steps of:
  adding to a medium a given *Lactobacillus rhamnosus* strain and a given *Lactobacillus paracasei* strain so that to obtain a composition with $LR_\alpha:LP_\alpha$ ratio higher or equal to 8:1
  or
  inoculating a fermentation medium with said given *Lactobacillus rhamnosus* strain and said given *Lactobacillus paracasei* strain and
  fermenting the inoculated medium by incubating it at a temperature suitable for growth of said strains, until the $LR_\alpha:LP_\alpha$ ratio is higher or equal to 8:1.

In a preferred embodiment of this process for preparing a composition, the $LR_\alpha:LP_\alpha$ ratio is as disclosed hereinabove.

In an embodiment, the process for preparing a composition comprises the step of adding to a medium a given *Lactobacillus rhamnosus* strain and a given *Lactobacillus paracasei* strain so that to obtain a composition with $LR_\alpha:LP_\alpha$ ratio higher or equal to 8:1. Each given strains are grown separately each under conditions suitable for its growth, then each given strain is added to a medium in a suitable quantity.

In another embodiment, the process for preparing a composition comprises the steps of inoculating a fermentation medium with said given *Lactobacillus rhamnosus* strain and said given *Lactobacillus paracasei* strain and fermenting the inoculated medium by incubating it at a temperature suitable for growth of said strains, until the $LR_\alpha:LP_\alpha$ ratio is higher or equal to 8:1. In this embodiment, the given strains are cofermented and the fermentation is carried out in order to obtain a suitable $LR_\alpha:LP_\alpha$ ratio in the fermentation medium at the end of the fermentation.

Preferably, the fermentation medium is milk.

The present invention also relates to the use of a composition of the invention in the manufacture of a composition for treatment of the human or animal body.

In a preferred embodiment, the composition of the invention is a fermented product, preferably a fermented dairy product.

There are various processes for preparing fermented product of the invention.

For example, a pre-composition comprising a given $LR_{\alpha'}:LP_{\alpha'}$ ratio may be added to a product already fermented in such a way that the $LR_\alpha:LP_\alpha$ ratio in the final product is as disclosed hereinabove. The pre-composition may be obtained by adding to a medium said given *Lactobacillus rhamnosus* strain and said given *Lactobacillus paracasei* strain or by co-fermenting said given *Lactobacillus rhamnosus* strain and said given *Lactobacillus paracasei* strain. Preferably, the product already fermented to which the pre-composition is added does not comprise said given *Lactobacillus rhamnosus* strain and said given *Lactobacillus paracasei* strain. Consequently, the $LR_{\alpha'}:LP_{\alpha'}$ ratio in the pre-composition may be the same as the $LR_\alpha:LP_\alpha$ ratio in the final fermented product.

Another way to prepare a fermented product according the invention may be to co-ferment said given *Lactobacillus rhamnosus* strain and said given *Lactobacillus paracasei* strain with the strains used to obtain the fermented product. For example, when the fermented product is a yoghurt, the strains used for the lactic fermentation are *Lactobacillus delbrueckii* subsp. *bulgaricus* and *Streptococcus thermophilus*, Thus, *Lactobacillus delbrueckii* subsp. *bulgaricus*, *Streptococcus thermophilus*, said given *Lactobacillus rhamnosus* strain and said given *Lactobacillus paracasei* strain may be co-fermented in order to obtain a yoghurt according to the invention.

The milkis generally first pasteurised before being fermented.

The pasteurisation step is a heating treatment at a temperature comprised between 72° C. and 138° C., preferably during 2 seconds to 30 minutes. Such a step and its conditions are well known to the one skilled in the art.

The fermentation step is preferably a lactic fermentation using techniques which are known to the skilled person.

When reference is made to a "lactic fermentation", this means an acidifying lactic fermentation which results in milk coagulation and acidification following the production of lactic acid which may be accompanied by the production of other acids, carbon dioxide and various substances such as exopolysaccharides (EPS) or aromatic substances, for example diacetyl and acetaldehyde.

To perform such a lactic fermentation, lactic ferments are added to the non-fermented dairy product, in particular milk, which has generally been pasteurized beforehand, and the temperature is kept between 25° C. and 44° C., preferably for 3 to 16 hours.

The invention will be further illustrated by the following FIGURES and examples. However, these examples and FIGURES should not be interpreted in any way as limiting the scope of the present invention.

FIGURES

FIG. 1 shows the effect of the administration of the following compositions on the gut barrier integrity protection in the DNBS-induced low-grade inflammation model of mice. The legend is as follow:
vehicule+PBS: mice not challenged with DNBS and not treated with probiotic strains
DNBS+PBS: mice challenged with DNBS and not treated with strains
DNBS+CNCM-13690: mice challenged with DNBS and treated with *L. rhamnosus* ($10^9$ CFU/ml)
DNBS+Mix 1:1: mice challenged with DNBS and treated with the same concentration ($10^9$ CFU/ml) of *L. rhamnosus* and *L. paracasei*
DNBS+Mix 1:10: mice challenged with DNBS and treated with the ratio of *L. rhamnosus:L. paracasei* 10:1 ($10^9$ CFU/ml: $10^8$ CFU/ml)
DNBS+CNCM-13689: mice challenged with DNBS and treated with *L. paracasei* ($10^9$ CFU/ml)

EXAMPLES

Material and Methods:
Bacterial Growth Conditions and Animals
*Lactobacillus rhamnosus* CNCM I-3690 and *Lactobacillus paracasei* CNCM I-3689 were grown in MRS medium (Difco, USA) under anaerobic conditions at 37° C.

Male C57BL/six mice (6-8 weeks old; Janvier, Le Genest Saint Isle, France) were maintained at the animal care facilities of the National Institute of Agricultural Research (IERP, INRA, Jouy-en-Josas, France) under specific pathogen-free (SPF) conditions. Mice were housed under standard conditions for a minimum of 1 week before experimentation. All experiments were performed in accordance with European Community rules for animal care and were approved by the relevant local committee (Comethea) (Protocol number 02550.0).

Experimental Design
Inflammation was induced as previously described (Laval et al., 2015). Briefly, mice where challenged under anaesthesia with a first intra-rectal dose of 100 mg/kg of dinitrobenzenesulfonicacid (DNBS) solution (ICN, Biomedical Inc.) in 30% ethanol (EtOH). Control mice (without colitis) received only 30% EtOH.

Thirteen days after the first DNBS injection, $10^9$ CFU of viable *Lactobacillus rhamnosus* CNCM I-3690 alone, $10^9$ CFU of viable *Lactobacillus rhamnosus* CNCM I-3690 and $10^9$ CFU of viable *Lactobacillus paracasei* CNCM I-3689 or $10^9$ CFU of viable *Lactobacillus rhamnosus* CNCM I-3690 and $10^8$ CFU of viable *Lactobacillus paracasei* CNCM I-3689 in 200 µl of PBS or PBS alone were administered intra-gastrically, daily for 10 days (gavage period).

Finally, 21 days after the first challenge, the mice were challenged again with a second administration of 50 mg/kg of DNBS or EtOH.

Weight loss was monitored during 3 days following the second DNBS injection to assess possible clinical signs of distress. To confirm the absence of over inflammation, colonic macroscopic and histological scores as well as colonic myeloperoxidase (MPO) activity (a marker of the degree of infiltration by polymorpho-nuclear neutrophils) and serum lipocalin-2 levels (an early inflammation marker) were determined as previously described (Shashidharamurthy et al., 2013; Martin et al., 2014; Laval et al., 2015).

Intestinal Permeability In Vivo
Permeability in vivo was assessed using fluorescein isothiocyanate-conjugated dextran (FITC-dextran 3000-5000 Da, Sigma-Aldrich) tracer as previously described (Tambuwala et al., 2010). Briefly, at the endpoint 0.6 mg/g body weight of FITC-dextran dissolved in PBS was administered to mice by oral gavage. To measure the presence of FITC-dextran in blood, 3.5 h after the gavage blood samples were recovered from the retro-orbital venous plexus and kept in dark at 4.0 until analysis. Mice were housed under standard conditions during this period with un-limited access to water and food. Serum was separated by centrifugation and plasma FITC levels were determined using a fluorescence microplate reader (excitation 485 nm and emission 530 nm; Tecan, Lyon, France).

Statistical Analysis
GraphPad software (GraphPad Sofware, LaJolla, Calif., USA) was used for statistical analysis. Results are presented as bar graphs or dot plots with means±SEM. Comparisons involved the non-parametric Kruskal-Wallistest followed by a Dunn's Multiple Comparison test. A p value of less than 0.05 was considered significant.

Results:
*L. rhamnosus* and *L. paracasei* strains were both tested in a chronic murine model of low-grade inflammation induced by two intrarectal administrations of dinitrobenzene sulfonic acid (DNBS) separated by a recovery period. This model is characterized by an increase of colon barrier permeability.

As shown in FIG. 1, *L. rhamnosus* CNCM-I-3690, but not *L. paracasei* CNCM-I-3689 is able to restore the integrity of the intestinal barrier. When the *L. rhamnosus* CNCM-1-3690 and the *L. paracasei* CNCM-I-3689 strains were mixed in the ratio 1:1, *L. rhamnosus* CNCM-I-3690 lost its capacity to protect the barrier but when in the mixture is at a ratio 10:1 where *L. paracasei* CNCM-I-3689 was present 10 times less than *L. rhamnosus* CNCM-I-3690, the *L. rhamnosus* CNCM-I-3690 beneficial effect is still present.

The invention claimed is:
1. A composition comprising:
a *Lactobacillus rhamnosus* CNCM I-3690 strain and
a *Lactobacillus paracasei* CNCM I-3689 strain
wherein the ratio of the *Lactobacillus rhamnosus* CNCM I-3690 strain to the *Lactobacillus paracasei* CNCM I-3689 strain ($LR_\alpha:LP_\alpha$) is between 9:1 and 15:1.
2. The composition according to claim 1 wherein the composition comprises at least $10^6$ Colony Forming Unit per ml (CFU/ml) of said given *Lactobacillus rhamnosus* strain.

3. The composition according to claim 1, wherein the composition comprises at least one additional *Lactobacillus paracasei* strain.

4. The composition according to claim 3, wherein the additional *Lactobacillus paracasei* strain is *Lactobacillus paracasei* CNCM I-1518.

5. The composition according to claim 1, wherein the composition is a food composition.

6. The composition according to claim 1, wherein the composition is a dairy product.

7. A method for improving the intestinal epithelial barrier integrity comprising administering to a subject the composition according to claim 1.

8. A method for treating a gastrointestinal disorder, type 1 diabetes or obesity comprising administering to a subject the composition according to claim 1.

9. The method according to claim 8, wherein the gastrointestinal disorder is an inflammatory bowel disease (IBD) and/or irritable bowel syndrome (IBS).

10. A process for preparing a composition comprising:
adding to a medium a *Lactobacillus rhamnosus* CNCM I-3690 strain and a *Lactobacillus paracasei* CNCM I-3689 strain to obtain a composition $LR_\alpha:LP_\alpha$ ratio between 9:1 and 15:1
or
inoculating a fermentation medium with the *Lactobacillus rhamnosus* CNCM I-3690 strain and the *Lactobacillus paracasei* CNCM I-3689 strain and
fermenting the inoculated medium by incubating it at a temperature suitable for growth of said strains, until the $LR_\alpha:LP_\alpha$ ratio is between 9:1 and 15:1.

* * * * *